United States Patent [19]

Drevline et al.

[11] Patent Number: 5,567,945
[45] Date of Patent: Oct. 22, 1996

[54] COMPACT ATOMIC ABSORPTION ANALYZER

[75] Inventors: Eric Drevline, Tariffville; Louis C. Burke, East Granby, both of Conn.

[73] Assignee: Analytical Precision, Inc., Tariffville, Conn.

[21] Appl. No.: 340,289

[22] Filed: Nov. 16, 1994

[51] Int. Cl.$^6$ .............................. G01J 3/42; G01J 3/443; G01N 21/71

[52] U.S. Cl. .................. 250/372; 250/341.6; 250/373; 250/428; 356/311; 356/312; 356/316

[58] Field of Search .................................... 250/372, 371, 250/373, 428, 339.06, 339.07, 339.12, 341.6; 356/311, 312, 316

[56] References Cited

U.S. PATENT DOCUMENTS

| | | | |
|---|---|---|---|
| 3,824,016 | 7/1974 | Woodriff et al. | 356/312 |
| 4,009,964 | 3/1977 | Bergen | 356/85 |
| 4,689,754 | 8/1987 | Collins et al. | 356/316 |
| 4,801,209 | 1/1989 | Wadlow | 356/311 |
| 5,303,026 | 4/1994 | Strobl et al. | 356/318 |

*Primary Examiner*—Constantine Hannaher
*Assistant Examiner*—Virgil O. Tyler
*Attorney, Agent, or Firm*—Fishman, Dionne & Cantor

[57] ABSTRACT

A compact atomic absorption analyzer includes a xenon flashlamp, processing circuits, optics, electronic heating apparatus and a photomultiplier. A sample to be tested is heated using electronic (radio frequency) heating apparatus within the optics to subject the sample to thermal energy sufficient to excite the element of the sample to a level at which it will radiate its characteristic line-emission spectra. A high intensity background light having an ultraviolet component is generated by the xenon flashlamp within the optics and this spectral distribution of this light is received by the photomultiplier. The output of the photomultiplier is processed by the processing electronics, with the results of the test displayed, stored and/or downloaded to an external computer or printer.

38 Claims, 9 Drawing Sheets

COMPACT ATOMIC ABSORPTION ANALYZER

BACKGROUND OF THE INVENTION

The present invention relates to spectroscopic analyzers. More particularly, the present invention relates to a spectroscopic analyzer which electronically heats a sample for detection by atomic absorption spectroscopy.

The field of spectroscopy is well known and relates to the measurement and interpretation of electromagnetic spectra arising from either emission or absorption of radiant energy by a substance. Spectroscopic analyzers are commonly used to analyze paint samples for detecting lead. It is well known that excessive levels of lead in the blood of children under six years of age can inhibit a child's learning ability. Ingestion of lead, or repeated exposure to even small amounts of lead over an extended period of time, can impair the physical and mental development of these young children and can also cause health related problems in adults. Excessive concentrations of lead in the body can seriously damage the central nervous system, brain, kidneys, red blood cells and in some cases cause death. Children often ingest lead due to its sweet taste. By way of example, a wet lollipop left on a window sill with chipping lead paint can absorb dangerous levels of lead, sufficient to cause permanent injury. A small chip (e.g. 50 mg. in size) is enough if ingested on a daily basis, over the course of several weeks to seriously poison a child. While the above discussion has been directed to lead based paint, other surface coating, such as glazes, are also known to contain toxic levels of lead. It is estimated that between one half to three quarters of the houses constructed in the United States prior to 1980 contain lead based paint. Most states have established laws requiring children to be tested for lead in accordance with minimum acceptable levels. Moreover, many states have passed laws requiring paint in multi-family dwellings and single family dwellings to be tested for lead when that dwelling is rented to a family having a young child or in some cases when a property is transferred.

SUMMARY OF THE INVENTION

The above-discussed and other drawbacks and deficiencies of the prior art are overcome or alleviated by the compact atomic absorption analyzer of the present invention. In accordance with the present invention the compact atomic absorption analyzer comprises a xenon flashlamp, processing circuits, optics, electronic heating means and a photomultiplier. The xenon flashlamp comprises a flash tube containing xenon gas, which produces an intense peak of radiant energy when a high pulsed voltage is applied between electrodes at opposite ends of the tube. The photomultiplier comprises a phototube with preferably ten dynodes between the photocathode and the output electrode. The photomultiplier detects the intensity level of impinging wavelength dependent radiation. A high intensity background ultraviolet light is generated by the xenon flashlamp within the optics and this spectral distribution of this light is received by the photomultiplier. Then a sample to be tested is heated using electronic (radio frequency) heating means within the optics whereby the sample is subjected to thermal energy sufficient to excite the element of the sample to a level at which it will radiate its characteristic line-emission spectra. For an atom or molecule in the ground electronic state to be excited to a higher electronic energy level, it must absorb energy via thermal collisions. Upon their return to a lower or ground electronic state, the excited atoms and molecules absorb the light background radiation characteristic of the sample components. The output of the photomultiplier is processed by the processing electronics, whereby the results of the test are displayed and/or downloaded to an external computer or printer.

BRIEF DESCRIPTION OF THE DRAWINGS

Referring now to the drawings wherein like elements are numbered alike in the several FIGURES.

DESCRIPTION OF THE PREFERRED EMBODIMENT

Figure 1:
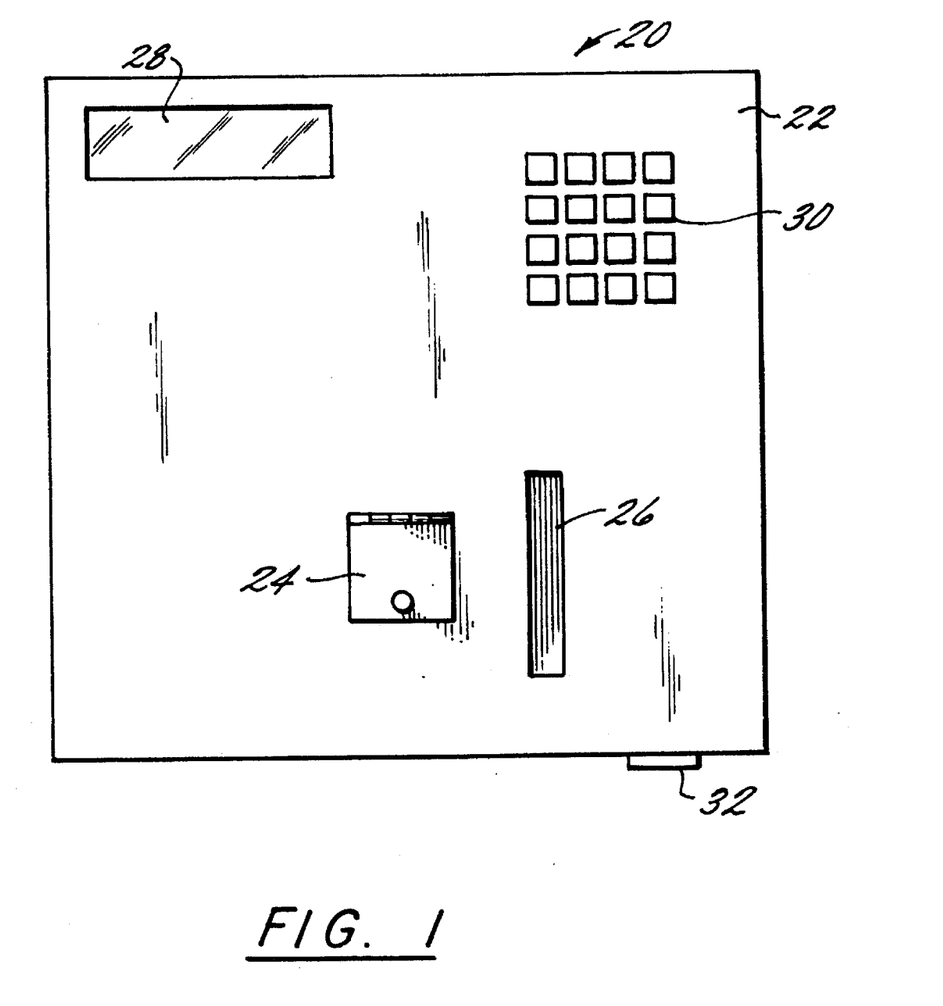
FIG. 1 is a diagrammatic plan view of the compact atomic absorption analyzer in accordance with the present invention.

Referring to FIG. 1, a spectroscopic analyzer in accordance with the present invention is shown generally at 20. Analyzer 20 comprises a housing 22 having an access cover 24 for allowing a sample to be analyzed to be deposited in analyzer 20, a slot 26 for insertion of a filter (described hereinafter), a display 28, a key pad 30, a RS-232 interface connector 32 (e.g., a DB9 connector), and electronics disposed within housing 22. Display 28 may comprise a 2×20 vacuum fluorescent display having a 8051 microcontroller, as is known. Display 28 provides a display of all relevant information regarding the identity of the specific reference sample and the corresponding sample being analyzed. Key pad 30 may comprise a 4×4 keypad and provides means for designating or selecting a test to be conducted in spectroscopic analyzer 20.

Figure 2:
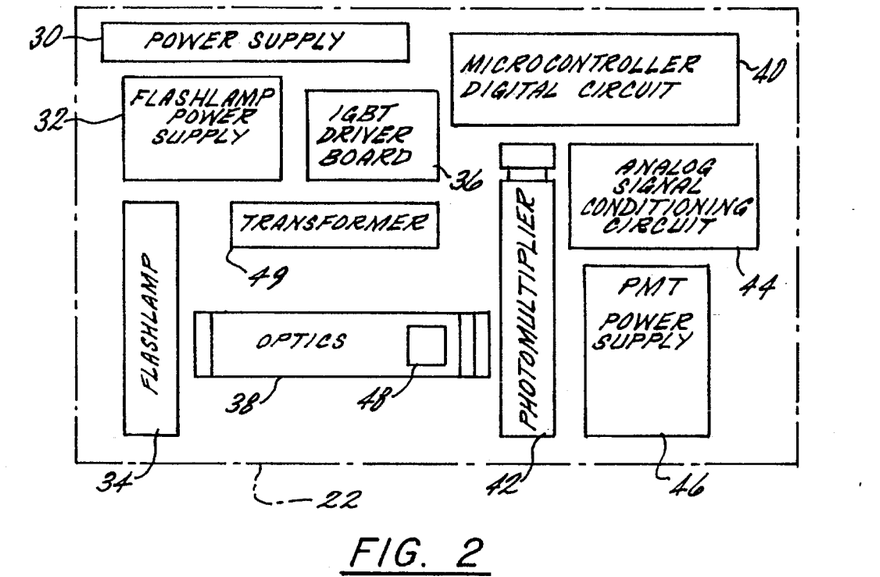
FIG. 2 is a diagrammatic view of the internal components of the compact atomic absorption analyzer of FIG. 1.

Referring to FIG. 2, disposed within housing 22 are a power supply 30, a flashlamp power supply 32, a xenon flashlamp 34, an integrator driver circuit 36, optics 38, a microcontroller digital circuit 40, a photomultiplier 42, an analog signal conditioning circuit 44 and a photomultiplier power supply 46. Xenon flashlamp 34 comprises a flash tube containing xenon gas, which produces a broad ban of radiant energy at wavelengths between 200–1,100 nanometers (nm) when a high D.C. (direct current) pulsed voltage, from a trigger transformer, at a low frequency (e.g., 3 Hz.) connected to power supply 32, is applied between electrodes at opposite ends of the tube. Flashlamp power supply 32 may comprise, for example, an E.G.&G. Electro Optics PC350 power supply utilizing an oil filled capacitor or a polypropylene mylar capacitor. Photomultiplier 42 comprises a phototube with one or more dynodes between the photocathode and the output electrode. Photomultiplier 42 detects the intensity level of impinging radiation which, may be, for example, 20 mV. The output of photomultiplier 42 is a low current signal which is convened by a load resistor to a voltage signal. This voltage signal being amplified and presented to the A/D (analog to digital) circuit.

Figure 3:
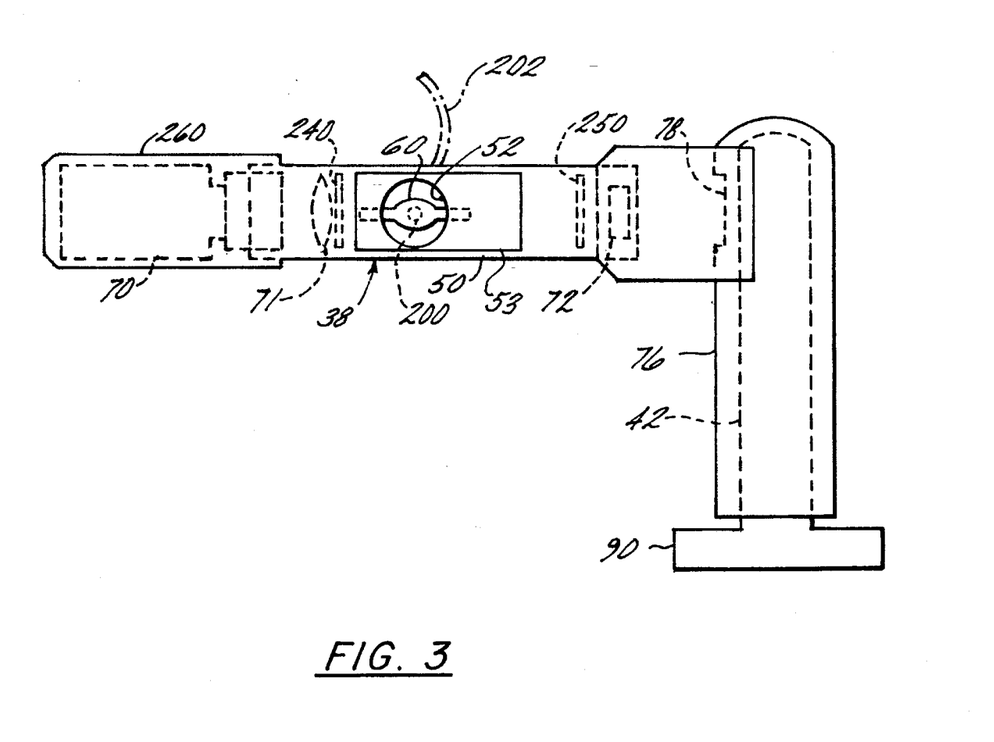
FIG. 3 is a diagrammatic view of the xenon flashlamp, the optics and the photomultiplier shown in FIG. 2.
Figure 4A:
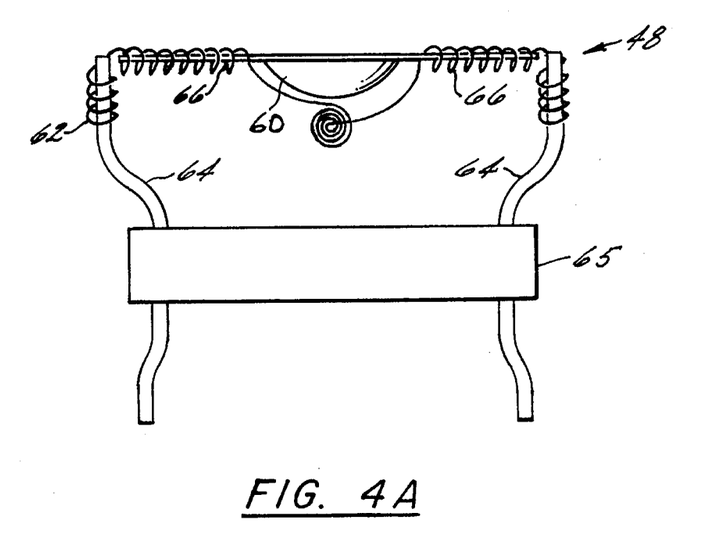
FIG. 4A is a diagrammatic view of the transformer and sample boat of the compact atomic absorption analyzer of FIG. 1.

Referring to FIGS. 3 and 4A, optics 38 comprises a light path chamber 50 is preferably comprised of an opaque material (e.g., aluminum) and includes an opening 52 for receiving a sample to be tested. Access to opening 52 is provided through a sliding door assembly 53 mounted on chamber 50. The sample is lowered through opening 52 into a titanium boat or receptacle 60. Receptacle 60 may be comprised of a material suitable for exposure to high temperatures (e.g., titanium or Kaplan D®). Receptacle 60 is electrically isolated from chamber 50 but is in thermal (infrared) contact with the super heated air within the chamber. Chamber 50 may include a valve whereby an inert gas could be entered. Chamber 50 also includes an air inlet opening 200 and an air outlet opening. The air outlet is to be attached to a vacuum by via a hose 202. The vacuum includes preferably a charcoal filter for capturing exhaust fumes for the device during use. Further, this flow of air around receptacle 60 significantly increases the rate of cooling after use, so that another sample can be analyzed more rapidly.

In the present example, a 25 kHz square wave at 84 volts (168 volt peak-to-peak) and up to 80 amps from insulated gate bipolar transistor (IGBT) full wave bridge (only one-half wave is shown) driver circuit 36 is applied to a coil 62 positioned a few millimeters from boat 60 which holds the sample. A transformer 49 having preferably a 2:1 ratio includes one winding thereof comprising a pair of heavy gauge copper wires 64, capable of handling high current, high temperature and high frequency, leading to extensions 66 of boat 60. Coil 62 disposed about the ends of wires 64 and extensions 66. Coil 62 is preferably comprised of a high temperature alloy, for example KAPLAN D®. An inductive energy pulse will emanate from coil 66 at a specified distance therefrom. This distance is designed to center the field of this inductive energy pulse generally on the longitudinal axis of the titanium boat 60. Temperatures generally greater than about 2500° F. can be achieved via this method. This coil 66 along with boat 60 are installed through an opening in chamber 50 so that boat 60 is positioned in alignment with opening 52 as described hereinabove. The distances are held by means of a ceramic machined cylinder 65 which includes the input from transformer 48.

Figure 4B:
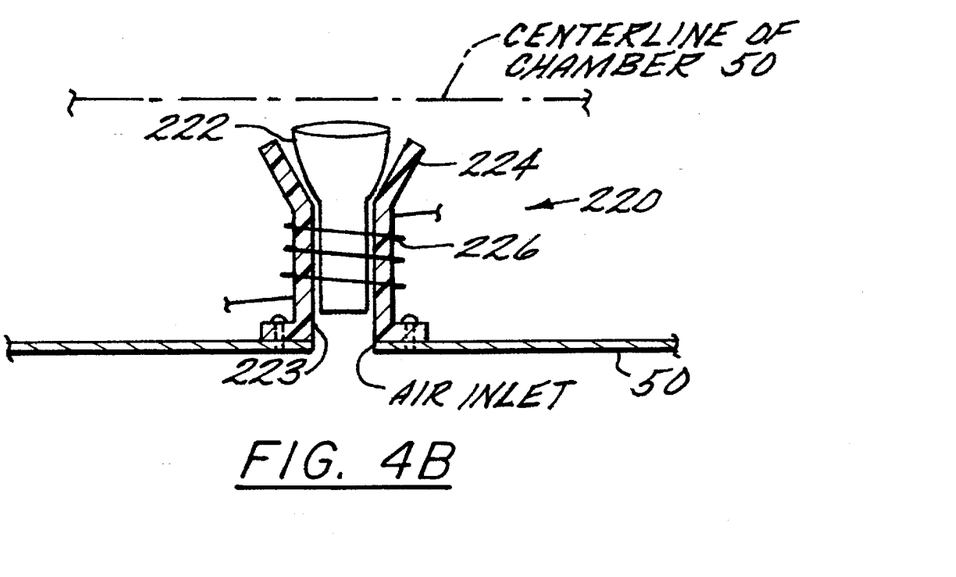
FIG. 4B is a diagrammatic sectional view of the receptacle/sample boat in accordance with an alternate embodiment.

Referring to FIG. 4B, an alternate embodiment of the receptacle is shown generally at 220. A tee shaped receptacle 222 is supported within an opening 223 of a ceramic (or other high temperature insulating material) funnel shaped support member 224. Receptacle 222 is easily removable, whereby it can readily be cleaned at regular intervals for continued long term use. Receptacle 222 may be comprised of a material suitable for exposures to high temperature (e.g., titanium or Kaplan D®). Further, receptacle 222 is electrically isolated from chamber 50 but is in thermal contact with the super heated air within the chamber. A coil 226 is disposed around the lower end of member 224 and is connected to the drive circuitry described above. Coil 226 is preferably comprised of a high temperature alloy, for example KAPLAN D®. Member 224 is secured to chamber 50 at the air inlet, whereby air will flow around receptacle 222 when drawn by the vacuum. Inductive energy emanating from coil 226 is centered about the receptacle whereby the sample therein is heated. Again, temperatures generally greater than about 2500° F. can be achieved via this method.

Figure 4C:
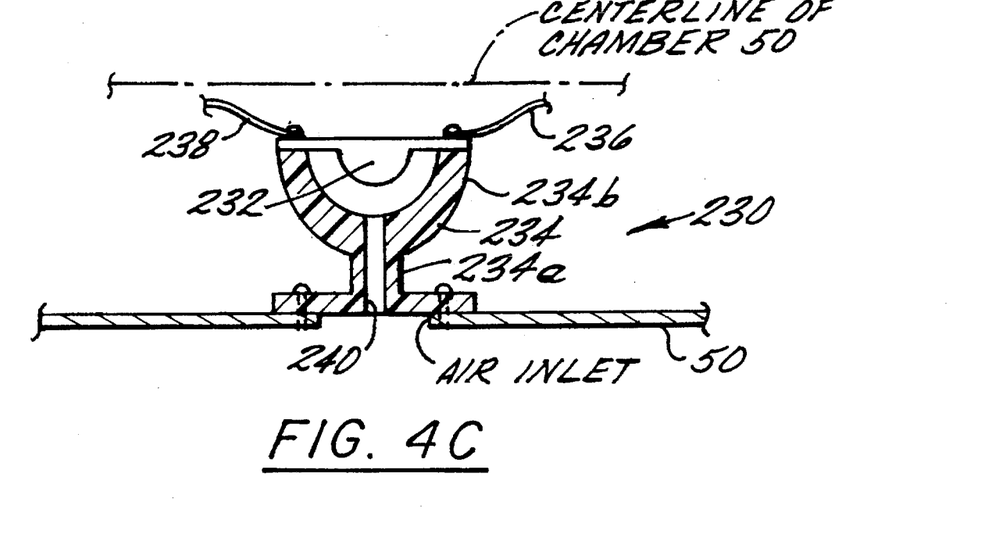
FIG. 4C is a diagrammatic sectional view of the receptacle/sample boat in accordance with yet another alternate embodiment.

Referring to FIG. 4C, still another alternate embodiment of the receptacle is shown generally at 230. A receptacle 232 (similarly shaped to receptacle 60) is supported by a ceramic (or other high temperature insulating material) support member 234. Receptacle 232 may be comprised of a material suitable for exposures to high temperature (e.g., titanium or Kaplan D®). Further, receptacle 232 is electrically isolated from chamber 50 but is in thermal contact with the super heated air within the chamber. Wires 236 and 238 are connected directly (without a coil) to receptacle 232 and the drive circuitry described above. It will be appreciated that a sufficient resistive load (e.g., 5 ohm, 250 W) is required with such direct connection. Member 234 comprises a lower pedestal shaped portion 234a and an upper bowl shaped portion 234b. Member 234 is secured to chamber 50 at the air inlet, whereby air will flow up through an opening 240 in member 234 and around receptacle 232 when drawn by the vacuum. Again, temperatures generally greater than about 2500° F. can be achieved via this method.

Xenon flashlamp 70 is fit tightly within an opening at one end of light path chamber 50 and oriented to direct light down the center of the light path. Light from flashlamp 70 is projected by a lens 71 disposed within chamber 50. A protective glass lens 240 is disposed within chamber 50 between lens 71 and receptacle 60 to protect lens 71 from the intense heat generated at receptacle 60. An access slot for allowing replacement of a narrow bandpass filter 72 (FIG. 5) to ascertain the different chemical concentrations is provided near the other end of chamber 50. Photomultiplier 42 is enclosed within a shield 76 (preferably of an EMI shielding material such as a μ-metal) which has an opening or window 78 aligned with the output end of chamber 50. It is preferred that all ambient light from the periphery of light path chamber 50 be eliminated to reduce any ambient light from eventually reaching photomultiplier 42. Along this line a cover 260 is disposed over flashlamp 70 and a portion of chamber 50. Cover 260 preferably has an internal reflective surface.

It is preferred that all effects from heat and electromagnetic interference are subtracted out, as will be described hereinafter. The heating effects are commonly referred to as the dark current. Software algorithms perform a zeroing function, whereby analyzer 20 reads a no sample condition (i.e., the voltage level with no sample present) and stores the value. This zero crossing test is preferably performed at the beginning of the day, and any time that the ambient temperature conditions vary greatly. For example, if a paint test was performed during the winter on an unheated floor of a house and then subsequently taken to a boiler room in an industrial complex, a variation in the dark current of the photomultiplier would occur. The operator preferably, prior to the test in the boiler room, calibrates the analyzer whereby either standards are analyzed in the chamber 50 or a zero crossing test is performed.

Figure 5:
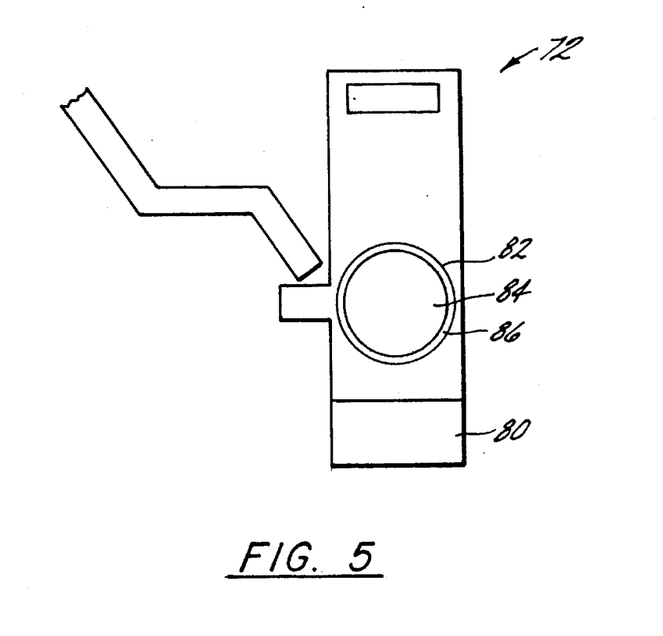
FIG. 5 is a diagrammatic view of the filter replacement cartridge of the compact atomic absorption analyzer of FIG. 1.

Referring to FIG. 5, filter replacement cartridge 72 includes a rectangular plastic window 80 closed at the bottom thereof with an opening 82 therethrough. A filter 84 is preferably cased in a plastic or aluminum washer type holder 86 which fits in opening 82. Cartridge 72 fits down past the bottom of light path chamber 50 with filter 84 centered along the optical axis of light path chamber 50.

Figure 6:
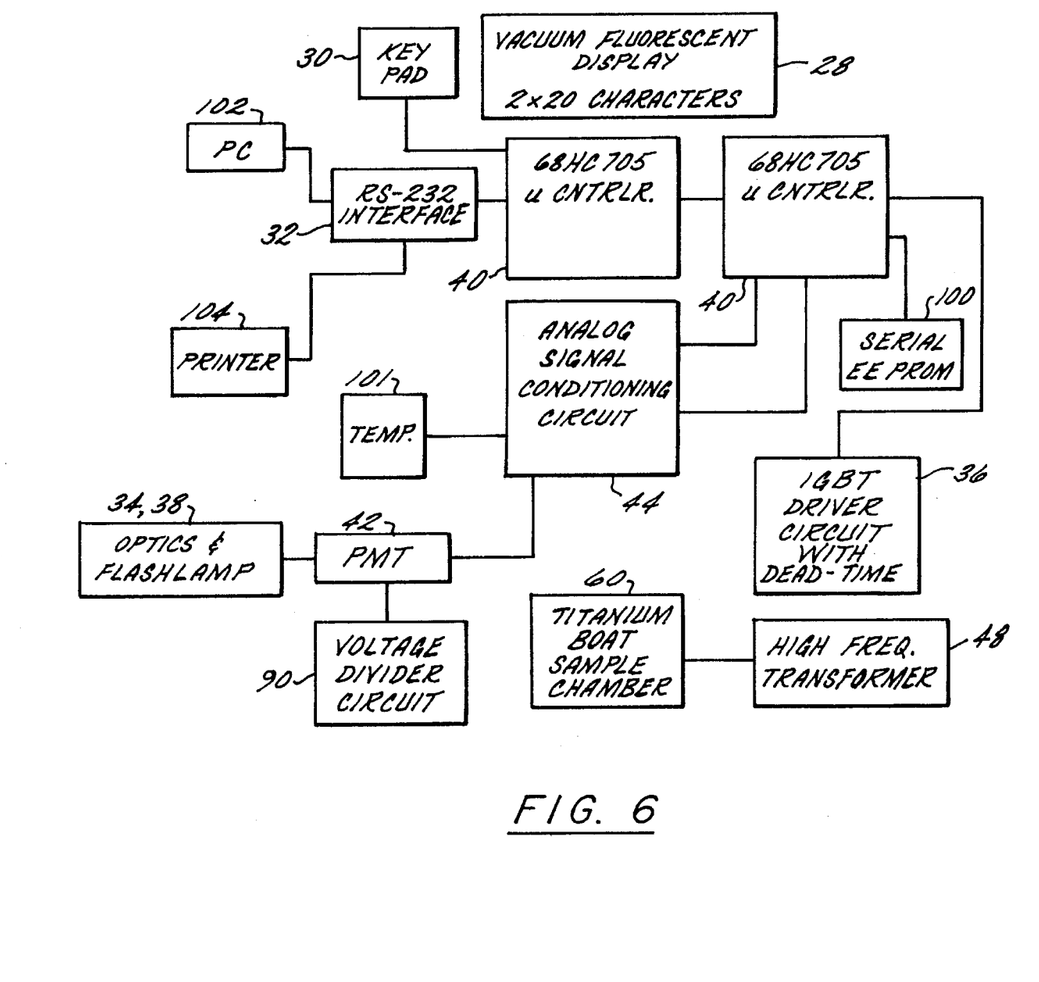
FIG. 6 is an electronic block diagram for the compact atomic absorption analyzer of FIG. 1.
Figure 7:
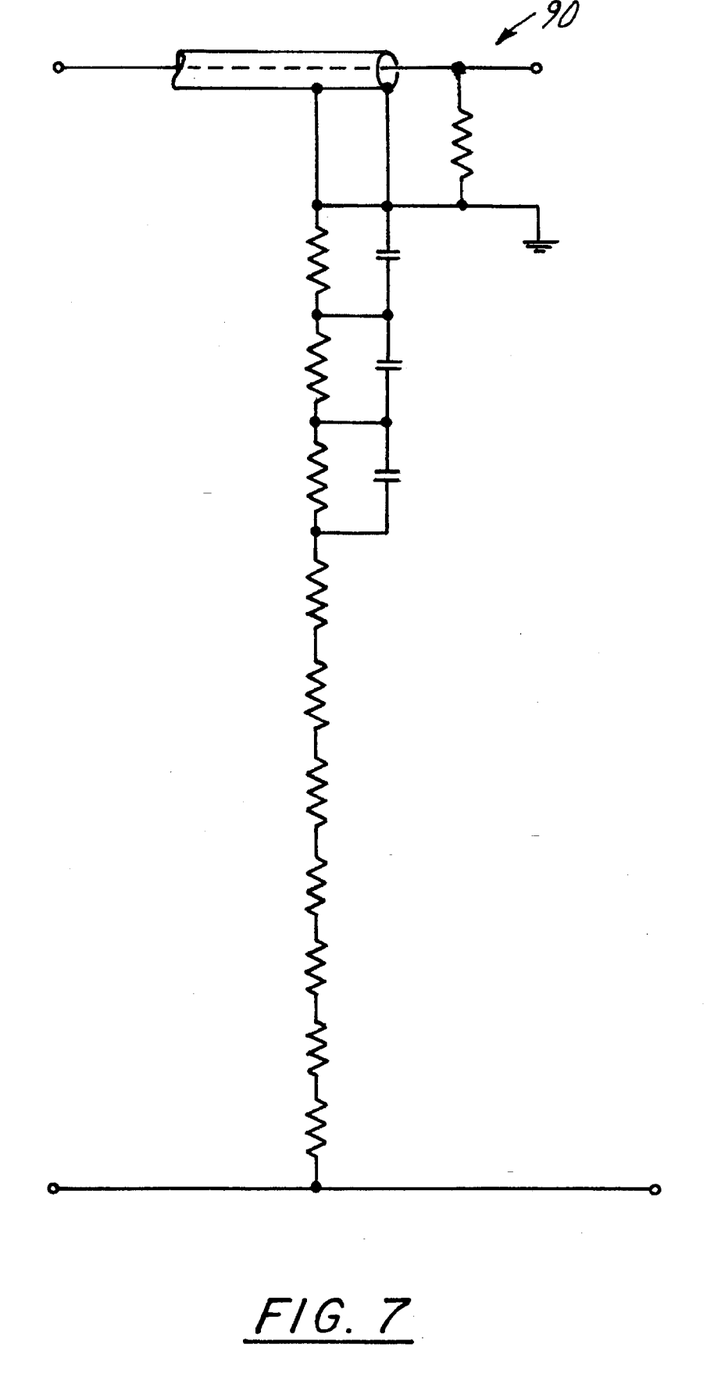
FIG. 7 is a schematic diagram of the voltage divider circuit shown in FIG. 6.
Figure 8:
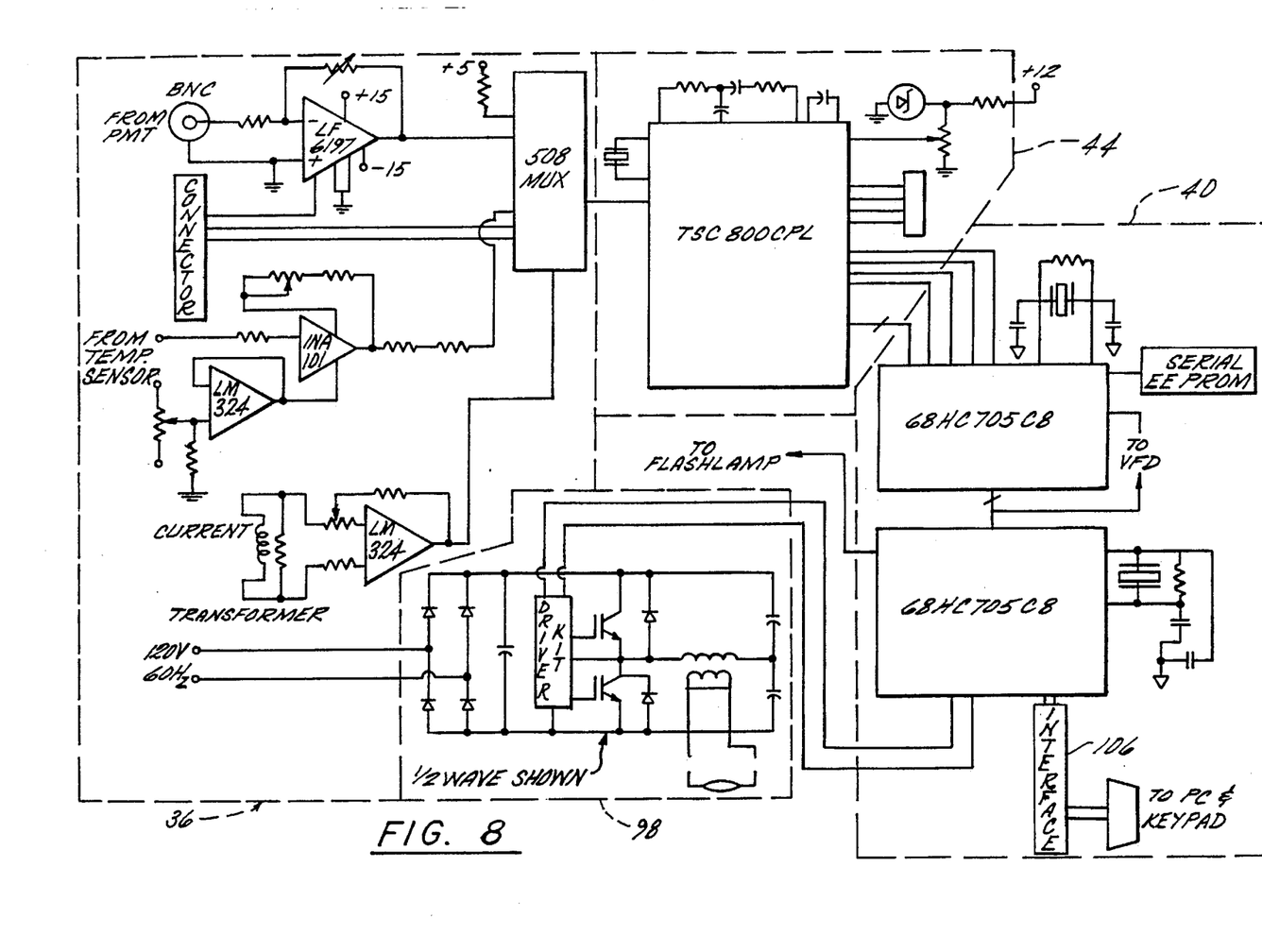
FIG. 8 is a schematic diagram of the electronics shown in FIG. 6.
Figure 9:
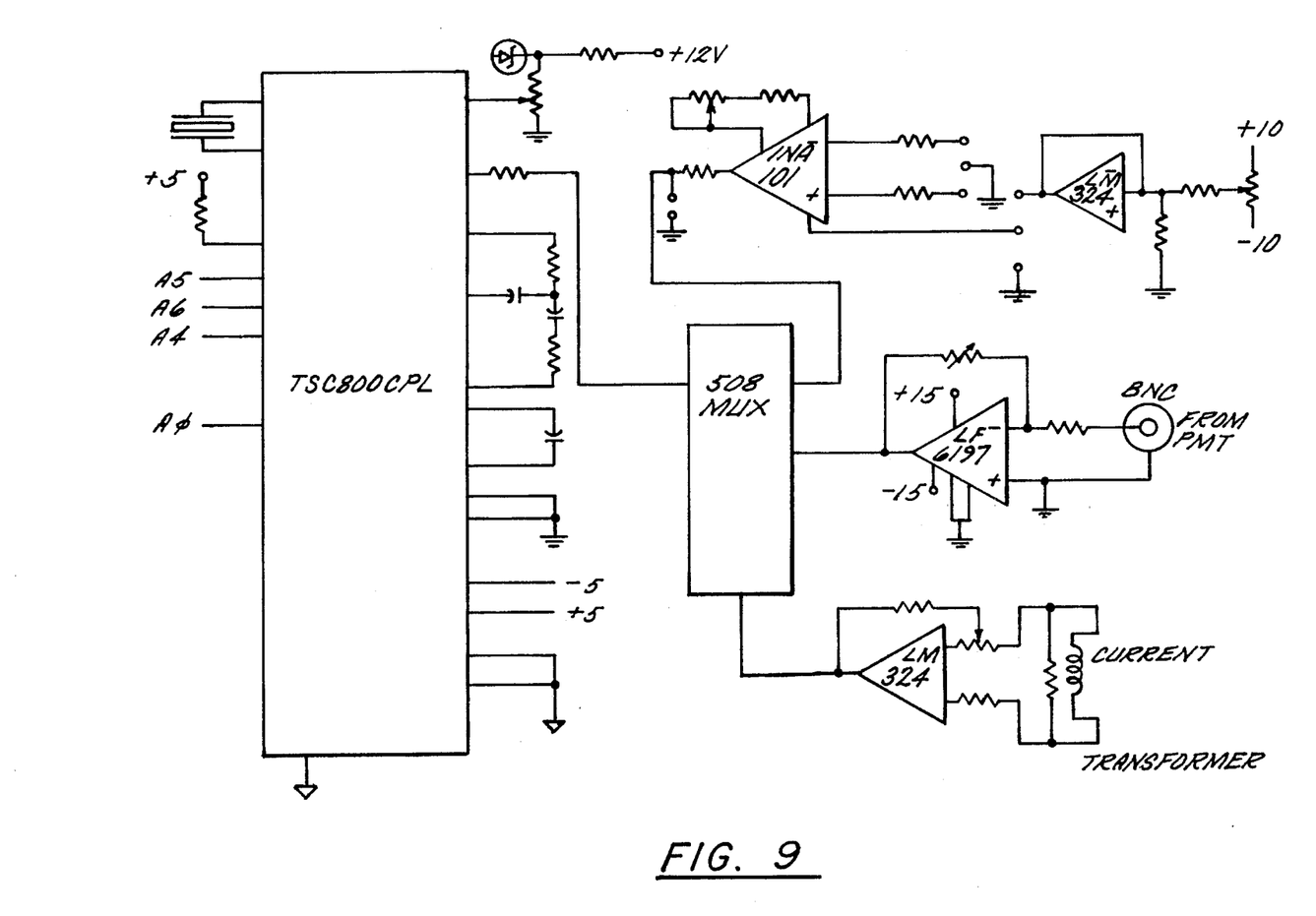
FIG. 9 is a schematic diagram of the analog conditioning circuit shown in FIG. 6.

Referring now to FIG. 6, an electronic block diagram for analyzer 20 is shown. A voltage divider circuit 90, a schematic diagram of which is shown generally in FIG. 7, comprises a resistor and capacitor circuit connected between shielded lines 92 and 94 which are connected to the dynodes of photomultiplier 42. The resistors of the voltage divider network are preferably precession resistor (e.g., 1% or 2% tolerance) which assures that the voltage drops from dynode to dynode are about 10% of the high voltage from power supply 46, which is adjusted to about −800 volts. An output signal from the voltage divider circuit 90 is presented to the input of the sample and hold integrator circuit of the A/D conditioning circuit 44, a schematic diagram of which is shown in FIG. 8, which stores the cumulative signal with minimal losses. The signal is then sent to analog to digital converter circuit 44, a schematic diagram of which is shown generally in FIG. 9, that samples and holds the signal for a fixed time interval (e.g., 10 times per second).

The driver circuit 98 of IGBT driver circuit 36 includes a dead-time generator, labeled driver kit and may for example comprise part number IXBD4412KIT commercially available from IXYS Corporation, for ensuring that both drivers cannot both on simultaneously. Microcontroller digital circuit 40 comprises a pair of microcontrollers, for example part number 68HC11 commercially available from Motorola Semiconductor. These microcontrollers include sample and hold amplifiers, an analog signal multiplexer, and a high speed analog to digital converter with 12-bit resolution. One of the microcontrollers is dedicated to outside communication (i.e., serial keypad 30, serial display 38, and interface 32. This microcontroller is connected to a serial EEPROM 100 which stores the data along with the time and date of recorded data. These two microcontrollers share a common 8-bit parallel bus which also interfaces with vacuum fluorescent display 28 to aid in debugging the microcontrollers and provide a user display. The bus is preferably transportable to any DOS environment. A four channel multiplexer 106 for the photomultiplier output signal, a current sensor signal from the secondary winding of transformer 48, and an output signal from a temperature sensor 101 (e.g., part number AD590 commercially available from Analog Devices) mounted inside the sample chamber. Transformer 48 includes closed loop feedback circuit with integrator driver circuit 36. A shunt resistor may be used to convert the current to a suitable voltage.

A computer (e.g., an XT compatible computer), not shown, may be included within housing 22 or more preferably the RS-232 interface 32 is employed to provide interfacing with an external computer 102. If an external computer is used, the spectroscopic analyzer 20 can be run as a stand alone system acquiring data and storing it in electrically erasable programmable read only memory (EEPROM) 100. This data can be stored virtually indefinitely and downloaded to an external computer 102 or printer 104 through the RS-232 interface 32. Preferably, code is downloaded from ROM (read only memory) of the microcontrollers to an external computer 102 and initiated upon boot up.

Alternatively, a circuit board having a connector compatible with, for example, an IBM-AT expansion bus is utilized and includes an analog to digital converter, instrumentation amplifiers, relay drivers, and bus decoding electronics. With this approach, the data processing and data storage capabilities of the computer can be utilized, however, the spectroscopic analyzer cannot be operated in a stand alone mode and must be connected to the computer during operation.

A computer program including control and user interface code for spectroscopic analyzer 20 is described hereinbelow. Written statements are for personal computer (PC) monitors and display messages are for display 28. The data can be presented via tables and bar graphs and/or converted to a spreadsheet type software, such as Labview or MS Excell.

Figure 10:
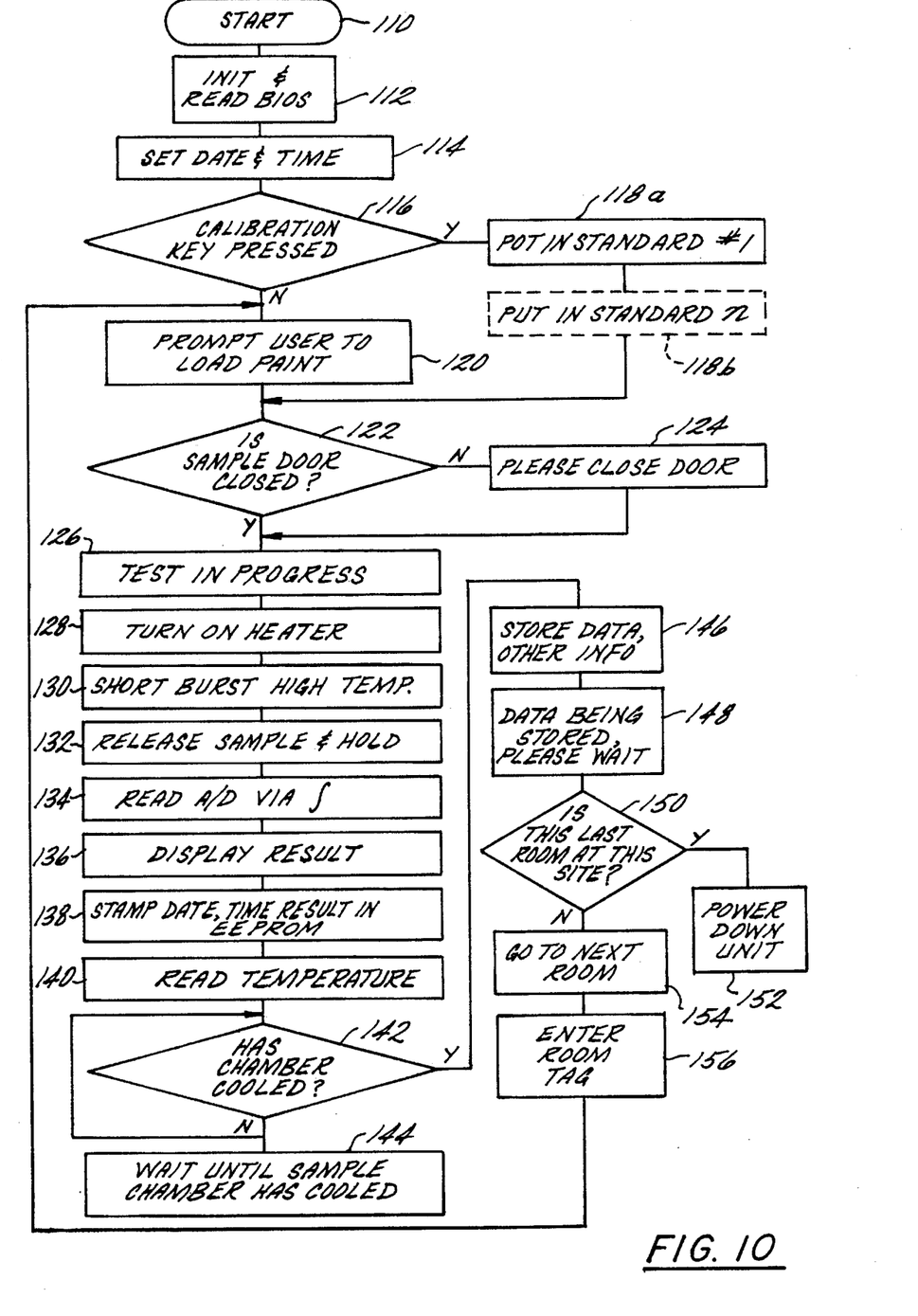
FIG. 10 is a flow chart for the compact atomic absorption analyzer of FIG. 1.

Referring to FIG. 10, a flow chart for analyzer 20 is shown. Analyzer 20 is powered on 110 and the system is initiated 112. The time and date are entered 114. Analyzer 20 is calibrated 116 for various standards 118a, 118b. Analyzer 20 then prompts user to load a sample 120. Sample door must be closed 122, otherwise the user in prompted to close the sample door 124. Thereafter, test in progress is displayed 126. Electronic heating is initiated 128 and a short burst of high temperature is applied to the sample 130. The signal (approximately 100 ms in duration) is detected and the data is held 132. This data is then A/D converted and integrated to produce a result 134 which is displayed 136. A time, date and sample location are associated with the results and stored in the EEPROM 138. The chamber temperature is sensed 140 and compared to see if the temperature in the chamber has cooled 142, if not a display is provided indicating that the user must wait until the temperature cools to a predetermined level 144. All data relative to this analysis is stored 146 and such is displayed 148, The user is prompt as to whether other test are to be performed 150, if not the unit will shut down 152. Otherwise a next location will be prompted 154 and identified 156 and the user will be prompted to enter the next sample 120.

In general, a solution of the sample or a direct sample scraped off the wall or taken from the soil is deposited (which may be combined with other chemicals) in titanium boat 60. The sample is then heated using electronic (radio frequency or infrared) heating whereby the sample is subjected to thermal energy sufficient to excite the element of the sample to a level at which it will radiate its characteristic line-emission spectra. For an atom or molecule in the ground electronic state to be excited to a higher electronic energy level, it must absorb energy via thermal collisions. Upon their return to a lower or ground electronic state, the excited atoms and molecules emit radiation characteristic of the sample components. A high intensity background light having an ultraviolet component is generated by xenon flashlamp 34. This spectral distribution of this light, approximately 200 nm to 1.1 μm, is received by the photomultiplier 42 and then stored. With a lead paint sample, after standard lead concentrations are established, the sample is volatized by radio frequency heating in the light path within the light path chamber 50 and another reading is taken. The sample will absorb light at a given wavelength (e.g., 283.3 nm for lead) in the light path. Therefore, a large amount of lead sample will read an appreciable level of light less than the straight xenon light.

A reference intensity level is established and compared to the detected intensity level. An appropriate filter 72 is employed so that spectroscopic analysis is undertaken at a selected wave length of the electromagnetic spectrum. The results are transmitted to display 28 and are also stored in memory 100, to be down loaded to a computer 102 for further analysis and processing.

Standards are preferably run on the spectroscopic analyzer on a daily basis to generate standards and create a calibration curve. The standards are composed of 99.9% lead, 50%, 25%, 5%, 1%, and 0.005%, however, not all these standards are required but it is preferred that at least three of them are run daily. The 0.005% standard is used to test low end sensitivity of the system. This information allows for more accurate results and also improves low end sensitivity. Spectroscopic analyzer 20 includes complete diagnostic self test capabilities. The standards for this protocol preferably contain a sample at the lowest anticipated and necessary level. A trade-off exist between signal processing gain/sensitive and range of sample detection. By way of example, with blood samples the sensitivity is enhanced at the expense of the range.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A spectroscopic analyzer comprising:
   a receptacle for receiving a sample to be analyzed;
   electronic heating means for subjecting a sample received in said receptacle to thermal energy sufficient to excite an element of the sample to a level at which the element radiates a line-emission spectra characteristic of the element;
   a light source for generating a light beam having an ultraviolet component, said receptacle being disposed within a path of said light beam wherein said line-emission spectra combines with said light beam generating a spectral distribution of light;
   a photomultiplier positioned within said path for receiving said spectral distribution of light and providing a spectral signal indicative thereof; and
   signal processing means for processing said spectral signal to provide a processed signal indicative of the element of said sample.

2. The spectroscopic analyzer of claim 1 wherein said receptacle is comprised of titanium.

3. The spectroscopic analyzer of claim 1 wherein said electronic heating means comprises radio frequency heating means.

4. The spectroscopic analyzer of claim 3 wherein said radio frequency heating means comprises:
   a transformer for generating a field of inductive energy generally centered about a longitudinal axis of said receptacle.

5. The spectroscopic analyzer of claim 1 further comprising:
   means for cooling said receptacle by directing air flow about said receptacle.

6. The spectroscopic analyzer of claim 1 further comprising:
   an insulating support member, said receptacle disposed on said support member.

7. The spectroscopic analyzer of claim 6 wherein said electronic heating means comprises:
   a coil for generating a field of inductive energy generally centered about said receptacle.

8. The spectroscopic analyzer of claim 1 wherein:
   said light source comprises a flashlamp; and
   said light beam comprises a band of radiant energy.

9. The spectroscopic analyzer of claim 8 wherein:
   said flashlamp comprises a xenon flashlamp; and
   said band of radiant energy having wavelengths between about 200 nanometers and about 1,100 nanometers.

10. The spectroscopic analyzer of claim 1 further comprising:
    a light path chamber having said light source disposed at one end thereof and said photomultiplier disposed at the other end thereof, said light path chamber having said receptacle disposed therein.

11. The spectroscopic analyzer of claim 10 wherein said light path chamber is comprised of an opaque material.

12. The spectroscopic analyzer of claim 1 further comprising:
    a housing having said receptacle, said electronic heating means, said light source, said photomultiplier and said signal processing means disposed therein, whereby said spectroscopic analyzer is a single portable unit.

13. The spectroscopic analyzer of claim 1 wherein said signal processing means further comprises:
    memory means for storing said processed signal.

14. The spectroscopic analyzer of claim 13 further comprising:
    interfacing means for downloading said processed signal from said memory means to an external device.

15. The spectroscopic analyzer of claim 14 wherein the external device is a computer.

16. The spectroscopic analyzer of claim 14 wherein the external device is a printer.

17. The spectroscopic analyzer of claim 1 further comprising:
    a display responsive to said processed signal for displaying characters identifying characteristics of the element.

18. The spectroscopic analyzer of claim 1 further comprising:
    a keypad for controlling functions of said spectroscopic analyzer.

19. The spectroscopic analyzer of claim 1 further comprising:
    a filter disposed within said path for filtering said spectral distribution of light received by said photomultiplier.

20. The spectroscopic analyzer of claim 1 wherein said electronic heating means further comprises:
    an insulated gate bipolar transistor driver circuit for high frequency heating.

21. A spectroscopic analyzer comprising:
    a light path chamber having opposing ends;
    a receptacle for receiving a sample to be analyzed, said receptacle disposed within said light path chamber;
    radio frequency heating means for subjecting a sample received in said receptacle to thermal energy sufficient to excite an element of the sample to a level at which the element radiates a line-emission spectra characteristic of the element;
    a flashlamp for generating radiant energy, said flashlamp disposed at one of said ends of said light path chamber, said line-emission spectra combines with said radiant energy within said light path chamber generating a spectral distribution of light therein;
    a photomultiplier disposed at the other one of said ends of said light path chamber for receiving said spectral distribution of light and providing a spectral signal indicative thereof; and
    signal processing means for processing said spectral signal to provide a processed signal indicative of the element of said sample.

22. The spectroscopic analyzer of claim 21 wherein said radio frequency heating means comprises:

a transformer for generating a field of inductive energy generally centered about a longitudinal axis of said receptacle.

23. The spectroscopic analyzer of claim 21 further comprising:

means for cooling said receptacle by directing air flow about said receptacle.

24. The spectroscopic analyzer of claim 21 further comprising:

an insulating support member, said receptacle disposed on said support member.

25. The spectroscopic analyzer of claim 24 wherein said electronic heating means comprises:

a coil for generating a field of inductive energy generally centered about said receptacle.

26. The spectroscopic analyzer of claim 21 further comprising:

a housing having said light path chamber, said receptacle, said radio frequency heating means, said flashlamp, said photomultiplier and said signal processing means disposed therein, whereby said spectroscopic analyzer is a single portable unit.

27. The spectroscopic analyzer of claim 21 wherein said signal processing means further comprises:

memory means for storing said processed signal.

28. The spectroscopic analyzer of claim 27 further comprising:

interfacing means for downloading said processed signal from said memory means to an external device.

29. The spectroscopic analyzer of claim 21 further comprising:

a display responsive to said processed signal for displaying characters identifying characteristics of the element.

30. The spectroscopic analyzer of claim 21 further comprising:

a keypad for controlling functions of said spectroscopic analyzer.

31. The spectroscopic analyzer of claim 21 further comprising:

a filter disposed within said light path chamber for filtering said spectral distribution of light received by said photomultiplier.

32. The spectroscopic analyzer of claim 21 wherein said radio frequency heating means further comprises:

an insulated gate bipolar transistor driver circuit for high frequency heating.

33. A method of spectroscopically analyzing a sample, comprising the steps of:

receiving a sample to be analyzed;

electronically heating the sample received to excite an element of the sample to a level at which the element radiates a line-emission spectra characteristic of the element;

combining said line-emission spectra with an ultraviolet light beam generating a spectral distribution of light;

receiving said spectral distribution of light and providing a spectral signal indicative thereof; and processing said spectral signal to provide a processed signal indicative of the element of said sample.

34. The method of claim 33 further comprising the steps of:

storing said processed signal.

35. The method of claim 34 further comprising the steps of:

downloading said stored processed signal to an external device.

36. The method of claim 33 further comprising the step of:

in response to said processed signal, displaying characters identifying characteristics of the element.

37. The method of claim 33 further comprising the step of:

filtering said spectral distribution of light.

38. The method of claim 33 wherein said step of electronically heating the sample comprises electrically heating at least about 25 kHz.

\* \* \* \* \*

UNITED STATES PATENT AND TRADEMARK OFFICE
CERTIFICATE OF CORRECTION

PATENT NO. : 5,567,945
DATED : October 22, 1996
INVENTOR(S) : Eric Drevine et al.

It is certified that error appears in the above-identified patent and that said Letters Patent is hereby corrected as shown below:

Column 3,
Line 14, delete "convened" and insert therefor -- converted --

Signed and Sealed this

Eleventh Day of February, 2003

JAMES E. ROGAN
*Director of the United States Patent and Trademark Office*